United States Patent
Henriksen et al.

(10) Patent No.: US 6,576,264 B1
(45) Date of Patent: *Jun. 10, 2003

(54) INSOLUBLE DRUG DELIVERY

(75) Inventors: Inge B Henriksen, Durham, NC (US); Awadesh K. Mishra, Durham, NC (US); Gary W. Pace, Durham, NC (US); Keith P. Johnston, Austin, TX (US); Simon Mawson, Austin, TX (US)

(73) Assignees: SkyePharma Canada Inc., Quebec (CA); Board of Regents, The University of Texas System, Austin, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/202,504

(22) PCT Filed: Oct. 17, 1996

(86) PCT No.: PCT/US96/16841
§ 371 (c)(1),
(2), (4) Date: Mar. 12, 1999

(87) PCT Pub. No.: WO97/14407
PCT Pub. Date: Apr. 24, 1997

Related U.S. Application Data
(60) Provisional application No. 60/005,340, filed on Oct. 17, 1995.

(51) Int. Cl.[7] .................................................. A61K 9/16
(52) U.S. Cl. ....................... 424/490; 424/494; 424/496; 424/497; 424/498; 424/489
(58) Field of Search ................................ 424/400, 489, 424/500, 501, 490–498; 264/4.1, 4.3, 4.6, 450

(56) References Cited

U.S. PATENT DOCUMENTS

| | | | |
|---|---|---|---|
| 2,803,582 A | 8/1957 | Cherney | |
| 3,137,631 A | 6/1964 | Soloway | |

(List continued on next page.)

FOREIGN PATENT DOCUMENTS

| | | |
|---|---|---|
| DE | 2 513 797 | 10/1975 |
| DE | 2 938 807 | 11/1980 |

(List continued on next page.)

OTHER PUBLICATIONS
International Journal of Pharmaceuticals, vol. 94, 1993, pp. 1–10, XP002027507 Phillips E.M. et al: "Rapid expansion from supercritical solutions: applications to pharmaceutical process" see p. 7—p. 8.

(List continued on next page.)

Primary Examiner—Gollamudi S. Kishore
(74) Attorney, Agent, or Firm—Leydig, Voit & Mayer, Ltd.

(57) ABSTRACT

Particles of water insoluble biologically active compounds, particularly water-insoluble drugs, with an average size of 100 nm to about 300 nm, are prepared by dissolving the compound in a solution then spraying the solution into compressed gaz, liquid or supercritical fluid in the presence of appropriate surface modifiers.

69 Claims, 7 Drawing Sheets

U.S. PATENT DOCUMENTS

| | | |
|---|---|---|
| 3,216,897 A | 11/1965 | Drantz |
| 3,274,063 A | 9/1966 | Nieper et al. |
| 3,594,476 A | 7/1971 | Merrill |
| 3,715,432 A | 2/1973 | Merrill |
| 3,755,557 A | 8/1973 | Jacobs |
| 3,794,476 A | 2/1974 | Michalik et al. |
| 3,937,668 A | 2/1976 | Zolle |
| 3,960,757 A | 6/1976 | Morishita et al. |
| 3,965,255 A | 6/1976 | Block et al. |
| 3,998,753 A | 12/1976 | Antoshkiw et al. |
| 4,016,100 A | 4/1977 | Suzuki et al. |
| 4,053,585 A | 10/1977 | Allison et al. |
| 4,056,635 A | 11/1977 | Glen et al. |
| 4,073,943 A | 2/1978 | Wretlind et al. |
| 4,078,052 A | 3/1978 | Papahadjopoulos |
| 4,089,801 A | 5/1978 | Schneider |
| 4,102,806 A | 7/1978 | Kondo et al. |
| 4,107,288 A | 8/1978 | Oppenheim et al. |
| 4,133,874 A | 1/1979 | Miller et al. |
| 4,145,410 A | 3/1979 | Sears |
| 4,147,767 A | 4/1979 | Yapel, Jr. |
| 4,186,183 A | 1/1980 | Steck et al. |
| 4,219,548 A | 8/1980 | Reller |
| 4,235,871 A | 11/1980 | Papahadjopoulos et al. |
| 4,241,046 A | 12/1980 | Papahadjopoulos et al. |
| 4,271,196 A | 6/1981 | Schmidt |
| 4,280,996 A | 7/1981 | Okamoto et al. |
| 4,298,594 A | 11/1981 | Sears et al. |
| 4,302,459 A | 11/1981 | Steck et al. |
| 4,308,166 A | 12/1981 | Marchetti et al. |
| 4,309,421 A | 1/1982 | Ghyczy et al. |
| 4,316,884 A | 2/1982 | Alam et al. |
| 4,320,121 A | 3/1982 | Sears |
| 4,325,871 A | 4/1982 | Sasaki et al. |
| 4,328,222 A | 5/1982 | Schmidt |
| 4,329,332 A | 5/1982 | Couvreur et al. |
| 4,331,654 A | 5/1982 | Morris |
| 4,332,795 A | 6/1982 | Ghyczy et al. |
| 4,332,796 A | 6/1982 | Los |
| 4,340,594 A | 7/1982 | Mizushima et al. |
| 4,345,588 A | 8/1982 | Widder et al. |
| 4,351,831 A | 9/1982 | Growdon et al. |
| 4,356,167 A | 10/1982 | Kelly |
| 4,369,182 A | 1/1983 | Ghyczy et al. |
| 4,378,354 A | 3/1983 | Ghyczy et al. |
| 4,394,372 A | 7/1983 | Taylor |
| 4,397,846 A | 8/1983 | Weiner et al. |
| 4,411,894 A | 10/1983 | Schrank et al. |
| 4,421,747 A | 12/1983 | Ghyczy et al. |
| 4,427,649 A | 1/1984 | Dingle et al. |
| 4,448,765 A | 5/1984 | Ash et al. |
| 4,483,847 A | 11/1984 | Augart |
| 4,485,054 A | 11/1984 | Mezei et al. |
| 4,492,720 A | 1/1985 | Mosier |
| 4,515,736 A | 5/1985 | Deamer |
| 4,529,561 A | 7/1985 | Hunt et al. |
| 4,532,089 A | 7/1985 | MacDonald |
| 4,610,868 A | 9/1986 | Fountain et al. |
| 4,613,505 A | 9/1986 | Mizushima et al. |
| 4,622,219 A | 11/1986 | Haynes |
| 4,675,236 A | 6/1987 | Ohkawara et al. |
| 4,687,762 A | 8/1987 | Fukushima et al. |
| 4,722,838 A * | 2/1988 | Tocker .................. 424/81 |
| 4,725,442 A | 2/1988 | Haynes |
| 4,756,910 A | 7/1988 | Yagi et al. |
| 4,761,288 A | 8/1988 | Mezei et al. |
| 4,762,720 A | 8/1988 | Jizomoto |
| 4,766,046 A | 8/1988 | Abra et al. |
| 4,776,991 A | 10/1988 | Farmer et al. |
| 4,801,455 A | 1/1989 | List et al. |
| 4,803,070 A | 2/1989 | Cantrell et al. |
| 4,806,350 A | 2/1989 | Gerber |
| 4,806,352 A | 2/1989 | Cantrell |
| 4,826,687 A | 5/1989 | Nerome et al. |
| 4,839,111 A | 6/1989 | Huang |
| 4,973,465 A | 11/1990 | Baurain et al. |
| 5,030,453 A | 7/1991 | Lenk et al. |
| 5,043,280 A * | 8/1991 | Fischer et al. |
| 5,091,187 A | 2/1992 | Haynes |
| 5,091,188 A | 2/1992 | Haynes |
| 5,100,591 A | 3/1992 | Leclef et al. |
| 5,145,684 A | 9/1992 | Liversidge et al. |
| 5,169,433 A | 12/1992 | Lindsay et al. |
| 5,246,707 A | 9/1993 | Haynes |
| 5,272,137 A | 12/1993 | Blasé et al. |
| 5,301,664 A * | 4/1994 | Sievers et al. |
| 5,302,401 A | 4/1994 | Liversidge et al. |
| 5,320,906 A | 6/1994 | Eley et al. |
| 5,340,564 A | 8/1994 | Illig et al. |
| 5,389,263 A * | 2/1995 | Gallagher et al. |
| 5,470,583 A | 11/1995 | Na et al. |
| 5,510,118 A | 4/1996 | Bosche et al. |
| RE35,338 E | 9/1996 | Haynes |
| 5,637,625 A | 6/1997 | Haynes |
| 5,770,559 A * | 6/1998 | Manning et al. |
| 5,776,486 A | 7/1998 | Castor et al. |
| 5,864,923 A * | 2/1999 | Rouanet et al. |
| 5,874,029 A * | 2/1999 | Subramaniam et al. |
| 5,922,355 A * | 7/1999 | Parikh et al. .................. 424/489 |
| 6,063,910 A * | 5/2000 | Debenedetti et al. |
| 6,177,103 B1 * | 1/2001 | Pace et al. |

FOREIGN PATENT DOCUMENTS

| | | | |
|---|---|---|---|
| EP | 0 052 322 | 5/1982 | |
| EP | 0 272 091 | 6/1988 | |
| EP | 0 322 687 | 7/1989 | |
| EP | 0 418 153 | 3/1991 | |
| EP | 0 456 670 | 11/1991 | |
| EP | 0 456 764 | 11/1991 | |
| EP | 0 499 299 | 8/1992 | |
| EP | 0 542 314 A | 5/1993 | |
| EP | 0 542 314 | 5/1993 | |
| EP | 0 601 618 | 6/1994 | |
| EP | 0 706 821 | 4/1996 | |
| EP | 0 744 992 B1 | 12/1996 | |
| GB | 2046094 | 11/1980 | |
| JP | 56167616 | 5/1980 | |
| JP | 55141407 | 11/1980 | |
| JP | 60208910 | 10/1985 | |
| JP | 63502117 | 8/1988 | |
| JP | 63233915 | 9/1988 | |
| JP | 1502590 | 7/1989 | |
| WO | WO 8500011 | 1/1985 | |
| WO | WO 8704592 | 8/1987 | |
| WO | WO8804924 | 7/1988 | |
| WO | WO 9104011 | 4/1991 | |
| WO | WO 91/15193 | * 10/1991 | ............ A61K/9/00 |
| WO | 91/15193 | * 10/1991 | ............ A61K/9/51 |
| WO | 95/01324 | * 1/1995 | |
| WO | WO 95/21688 | 8/1995 | |
| WO | WO9714407 | 4/1997 | |
| WO | WO9807414 | 2/1998 | |
| WO | WO9952504 | 10/1999 | |

OTHER PUBLICATIONS

Krukonis et al., "Supercritical Fluid Nucleation of Difficult–to–Comminute Solids" paper 140f, Annual Meeting, AIChE, San Francisco, 1984, 20 pages.

Tom et al., "Applications of Supercritical Fluids in the Controlled Release of Drugs", Supercritical Fluid Engineering Science, Chapter 19, pp. 238–257, 1993.

Chang et al., "Precipitation of Microsize Organic Particles from Supercritical Fluids", AIChE Journal, vol. 35, pp. 1876–1882, 1989.

Ross et al., "Aqueous Solutions of Surface–Active Solutes", *Collodial Systems and Interfaces*, © 1988, pp. 148–151.

Sande et al., "Antimicrobial Agents: Antifungal and Antiviral Agents", pp. 1219–1222.

Bittman, Robert, "Sterol–Polyene Antibiotic Complexation: Probe of Membrane Structure," *Lipids*, vol. 13, No. 10, pp. 686–691 (1978).

Mishra et al., "Scientifically Speaking: Novel Injectable Formulations of Water–Insoluble Drugs", *Controlled Release Newsletter*, vol. 17, Issue 2, Jun. 2000, pp. 21–30.

Bangham et al., "Diffusion of Univalent Ions Across the Lamellas of Swollen Phospholipids", *J. Mol. Biol.* (1965) 13, pp. 238–252.

Huang et al., "Interaction of the N–terminus of Sterol Carrier Protein 2 with Membranes: Role of Membrane Curvature", *Biochem. J*, 1999, vol. 8, pp. 593–603.

Gregoriadis, Gregory, "The Carrier Potential of Liposomes in Biology and Medicine", *New Engl. J. Med.*, 1976, vol. 295, No. 13, pp. 704–710.

Cudd et al., "Liposomes Injected Intravenously into Mice Associate with Liver Mitochondria, " Biochem. Biophys Acta, 1984, vol. 774, pp. 169–180.

Benz et al., "Electrical Capacity of Black Lipid Films and of Lipid Bilayers Made from Monolayers", *Biochem. Biophys. Acta*, 1975, vol. 394, pp. 323–334.

Goodman and Gillman's, "The Pharmacological Basis of Therapeutics," 7$^{th}$ Ed., *MacMillan Publishing Co.*, New York (1985), Chap. 15, p. 312.

Cherney, L.S., "Tetracaine Hydroiodide: A Long Lasting Local Anesthetic Agent for the Relief of Postoperative Pain", *Anesth. Analg.*, 1963, vol. 42, No. 4, pp. 477–481.

Haynes et al., "Metal–Ligand Interactions in Organic Chemistry and Biochemistry", B. Pullman and N. Goldblum (Eds.), part 2, 1977, pp. 189–212.

Haynes et al., "Ultra–Long Duration Local Anesthesia Produced by Injection of Lecithin–coated Methxyfluorene Microdroplets", *Aneshesiology*, 1985 vol. 63, No. 5, pp. 490–499.

Haynes et al., "Ultra–Long Duration Local Anesthesia Produced by Intra–Dermal Injection of Lecithin–Coated Methoxyflurane Microdroplets", *Proceed. Intern. Symp. Control. Rel. Bioact. Mater.*, 1987, vol. 14, pp. 293–294.

Kirkpatrick et al., "Local Anesthetic Efficacy of Methoxyflurane Microdroplets in Man," *Anesthesiology*, 1987, 67(3A), p. A254.

Wu et al., "Pharmacokinetics of Methoxyflurane After Its Intra–Dermal Injection as Lecithin–Coated Microdroplets," *Journal of Controlled Release* (in press), 1989, vol. 9, pp. 1–12.

Rompp's Chemie Lexikon (Dr. Hermann Rompp), "Emulsion", 2 Aufl., Bd. 1, 1950, Stuttgart.

Bergmann, Ludwig, *Der Ultraschall*, 5 Aufl., 1949, Stuttgart, S. 551–564, 672f.

D.J. Dixon, Ph.D., *Dissertation*, University of Texas at Austin.

Yeo et al., "Formation of Microparticulate Protein Powders using a Supercritical Fluid Anti–Solvent", *Biotechnol. and Bioeng.*, 1993, 341.

Randolph et al., "Micron Sized Biodegradeable Particles of Poly(L–latic Acid) via the Gas Anti–Solvent Spray Precipitation Process", *Biotechnology Progress*, 1993, vol. 9, p. 429.

Schmitt et al., "Finely–Divided Powders by Carrier Solution Injection into a Near or Supercritical Fluid", *Amer. Inst. Chem. Eng. J.*, 1995, vol. 41, pp. 2476–2486.

Donsi et al., "Possibility of Application to Pharmaceutical Field", Pharm. ACTA HELV, 1991, pp 170–73.

McHugh et al., "Supercritical Fluid Extraction" Principles and Practice, 2$^{nd}$ Ed. (1994).

\* cited by examiner

INSOLUBLE DRUG DELIVERY

This application is a 371 of PCT/US96/16841 filed Oct. 17, 1996 and claims priority over U.S. Ser. No. 60/005,340 filed Oct. 17, 1995.

This invention provides a novel process for producing sub-micron sized particles of water insoluble compounds with biological uses, particularly water insoluble drugs.

BACKGROUND AND SUMMARY OF THE INVENTION

Approximately one-third of the drugs in the United States Pharmacopoeia are water-insoluble or poorly water-soluble. Many currently available injectable formulations of such drugs carry important adverse warnings on their labels that originate from detergents and other agents used for their solubilization. Oral formulations of water-insoluble drugs or compounds with biological uses frequently show poor and erratic bioavailability. In addition, water-solubility problems delay or completely block the development of many new drugs and other biologically useful compounds.

Two alternative approaches for insoluble drug delivery are microparticles which involves forming a phospholipid stabilized aqueous suspension of submicron sized particles of the drug (see U.S. Pat. Nos. 5,091,187; 5,091,188 and 5,246,707) and microdroplets which involves forming a phospholipid stabilized oil in water emulsion by dissolving the drug in a suitable bio-compatible hydrophobic carrier (see U.S. Pat. Nos. 4,622,219 and 4,725,442).

The pharmacokinetic properties of both oral and injectable microparticle formulations are dependent on both the particle size and phospholipid surface modifier. However, with certain water insoluble compounds the current employed methods of particle size reduction are problematic. Thus, the overall objective of this invention is to develop a novel process based on the use of compressed fluids, including supercritical fluid technology, that yields surface modifier-stabilized suspensions of water insoluble drugs with an average particle size of 100 nm to about 300 nm and a narrow size distribution. The inventive process is robust, scalable and applicable to a wide range of water-insoluble compounds with biological uses.

BRIEF DESCRIPTION OF THE DRAWINGS

The invention is further explained with reference to the attached drawings in which.

DESCRIPTION OF THE INVENTION

Figure 1:
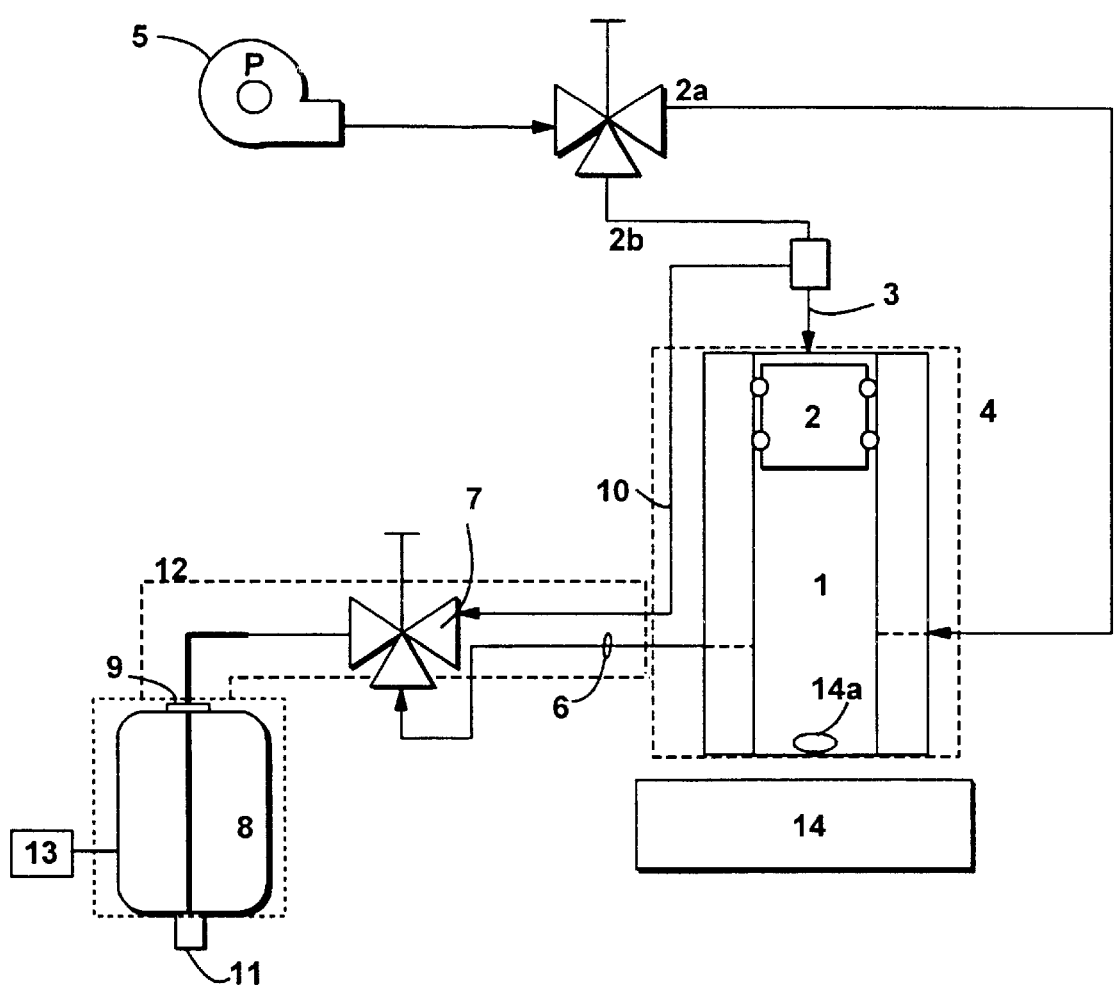
FIG. 1 is a schematic representation of an apparatus for carrying out the present invention by precipitating the bioactive substance by rapid expansion from a supercritical solution.

This invention is a process using compressed fluids to produce submicron sized particles of industrially useful poorly soluble or insoluble compounds with biological uses by: (1) precipitating a compound by rapid expansion from a supercritical solution (Rapid expansion from supercritical solution) in which the compound is dissolved, or (2) precipitating a compound by spraying a solution, in which the compound is soluble, into compressed gas, liquid or supercritical fluid which is miscible with the solution but is antisolvent for the compound. In this manner precipitation with a compressed fluid antisolvent (Compressed fluid antisolvent) is achieved. Optionally, the process combines or integrates a phospholipid in water or other suitable surface modifiers such as surfactants, as may be required, into the processes. The surfactant is chosen to be active at the compound-water interface, but is not chosen to be active at the carbon dioxide-organic solvent or carbon dioxide-compound interface when carbon dioxide is used as the supercritical solution. A unique feature of this invention is the combination of either rapid expansion from supercritical solution or compressed fluid antisolvent with recovery of surface modified stable submicron particles in an aqueous phase.

By industrially useful insoluble or poorly soluble compounds we include biologically useful compounds, imaging agents, pharmaceutically useful compounds and in particular drugs for human and veterinary medicine. Water insoluble compounds are those having a poor solubility in water, that is less than 5 mg/ml at a physiological pH of 6.5 to 7.4, although the water solubility may be less than 1 mg/ml and even less than 0.1 mg/ml.

Examples of some preferred water-insoluble drugs include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antarrhythmics, antihypertensive agents, antineoplastic agents, hormones, and nutrients. A detailed description of these and other suitable drugs may be found in *Remington's Pharmaceutical Sciences*, 18th edition, 1990, Mack Publishing Co. Philadelphia, Pa.

Cyclosporine, a water insoluble immunosuppressive drug, is used as a model to illustrate the invention. This drug was chosen since it has not been possible by using conventional size reduction techniques to achieve the particle size and distribution believed necessary to reach the desired pharmacokinetic performance.

Cyclosporine is a water insoluble, lipophilic 11 amino acid polypeptide with unique immunosuppressive properties. Its major use is as an immunosuppressant in solid organ transplantation. The clinical utility of the currently available pharmaceutical dosage forms are severely limited by the drug's insolubility. That is, the bioavailability of the oral form is low and the intra and inter patient absorption is variable.

The phospholipid may be any natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof The phospholipid may be salted or desalted, hydrogenated or partially hydrogenated or natural semisynthetic or synthetic.

Examples of some suitable second surface modifiers include: (a) natural surfactants such as casein, gelatin, tragacanth, waxes, enteric resins, paraffin, acacia, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxypropylcellulose, hydroxypropylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, and (e) colloidal clays such as bentonite and veegum. A detailed description of these surfactants may be found in *Remington's Pharmaceutical Sciences*, and Theory and Practice of Industrial Pharmacy, Lachman et al, 1986.

More specifically, examples of suitable second surface modifiers include one or combination of the following: polaxomers, such as PLURONIC™ F68, F108 and F127, which are block copolymers of ethylene oxide and propylene oxide available from BASF, and poloxamines, such as TETRONIC™ 908 (T908), which is a tetrafunctional block copolymer derived from sequential addition of ethylene oxide and propylene oxide to ethylene-diamine available from BASF, TRITON™ X-200, which is an alkyl aryl polyether sulfonate, available from Rohm and Haas. TWEEN™ 20, 40, 60 and 80, which are polyoxyethylene sorbitan fatty acid esters, available from ICI Speciality Chemicals, CARBOWAX™ 3550 and 934, which are polyethylene glycols available from Union Carbide, hydroxy propylmethylcellulose, dimyristoyl phosphatidylglycerol sodium salt, sodium dodecylsulfate, sodium deoxycholate, and cetyltrimethylammonium bromide.

Particles produced by the process of this invention are generally at most 500 nm in size usually below 300 nm, desirably less than 200 nm, preferably less than about 100 nm and often in a range of 0.1 to 100 nm in size. These particles are narrowly distributed in that 99% of the particles are below 500 nm and preferably below 400 nm with peaks at half width at half height at about 200 nm and preferably below 100 nm. The particles may be recovered from suspension by any convenient means such as spray drying, lyophilization, diafiltration, dialysis or evaporation.

The solvent properties of supercritical fluids are strongly affected by their fluid density in the vicinity of the fluid's critical point. In rapid expansion from supercritical solutions, a non volatile solute is dissolved in a supercritical fluid. Nucleation and crystallization are triggered by reducing the solution density through rapid expansion of the supercritical fluid to atmospheric conditions. To achieve this the supercritical fluid is typically sprayed through 10–50 microns (internal diameter) nozzles with aspect ratios (L/D) of 5–100. The fluid approaches sonic terminal velocity at the nozzle tip and high levels of supersaturation result in rapid nucleation rates and limited crystal growth. The combination of a rapidly propagating mechanical perturbation and high supersaturation is a distinguishing feature of rapid expansion from a supercritical solution. These conditions lead to the formation of very small particles with a narrow particle distribution.

The first comprehensive study of rapid expansion from a supercritical solution was reported by Krukonis (1984) [V. J. Krukonis: AIChE Annual Meeting San Francisco (1984), as cited in J. W. Tom et al.: *Supercritical Fluid Engineering Science*, Chapter 19, p238, (1993)] who formed microparticles of an array of organic, inorganic, and biological materials. Most particle sizes reported for organic materials, such as lovastatin, polyhydroxyacids, and mevinolin, were in the 5–100 micron range. In another study, particles of beta-carotene were formed by expansion of ethylene into a heated gelatin solution to inhibit post expansion particle aggregation. [Chang et al.: *AIChE Journal*, Vol. 35, pp. 1876–1882 (1989)]

Most rapid expansion from supercritical solution studies on organic materials utilize supercritical carbon dioxide. However, ethane was preferred to carbon dioxide for beta-carotene because of certain chemical interactions. Carbon dioxide is generally preferred, alone or in combination with a cosolvent. Minute additions of a cosolvent can increase the solubility of some solutes by orders of magnitude. When cosolvents are used in rapid expansion from a supercritical solution, care is required to prevent desolution of the particles due to solvent condensing in the nozzle. Normally, this is achieved by heating the supercritical fluid, prior to expansion, to a point where no condensate (mist) is visible at the nozzle tip.

A similar problem occurs when carbon dioxide is used alone. During adiabatic expansion (cooling), carbon dioxide will be in two phases unless sufficient heat is provided at the nozzle to maintain a gaseous state. Most investigators recognize this phenomenon and increase the pre-expansion temperature to prevent condensation and freezing in the nozzle. A significant heat input is required (40–50 kcal/kg) to maintain carbon dioxide in the gaseous state. If this energy is supplied by increasing the pre-expansion temperature the density drops and consequently reduces the supercritical fluid's solvating power. This can lead to premature precipitation and clogging of the nozzle.

There are a number of advantages in utilizing compressed carbon dioxide in the liquid and supercritical fluid states, as a solvent or anti-solvent for the formation of materials with submicron particle features. Diffusion coefficients of organic solvents in supercritical fluid carbon dioxide are typically 1–2 orders of magnitude higher than in conventional liquid solvents. Furthermore, carbon dioxide is a small linear molecule that diffuses more rapidly in liquids than do other antisolvents. In the antisolvent precipitation process, the accelerated mass transfer in both directions can facilitate very rapid phase separation and hence the production of materials with sub-micron features. It is easy to recycle the supercritical fluid solvent at the end of the process by simply reducing pressure. Since supercritical fluids do not have a surface tension, they can be removed without collapse of structure due to capillary forces. Drying, of the product is unusually rapid. No carbon dioxide residue is left in the product, and carbon dioxide has a number of other desirable characteristics, for example it is non-toxic, nonflammable, and inexpensive. Furthermore, solvent waste is greatly reduced since a typical ratio of antisolvent to solvent is 30:1.

As an antisolvent, carbon dioxide has broad applicability in that it lowers the cohesive energy of nearly all organic solvents. In 1992, D. J. Dixon, Ph.D. Dissertation, University of Texas at Austin, described a process in which liquid solutions of polymer in solvent are sprayed into compressed carbon dioxide to form microspheres and fibers. In this process, so called precipitation with a compressed fluid antisolvent, the polymer is insoluble in carbon dioxide, and the organic solvent is fully miscible with $CO_2$. This concept has been used to form biologically active insulin particles (4 microns) [Yeo, S. D., Lim, G. B. and Debenedetti, P. G. Formation of Microparticulate Protein Powders using a Supercritical Fluid Anti-Solvent, Biotechnol. and Bioeng. 1993, 341], several micron biodegradable L-poly(lactic acid) particles [Randolph, T. W. B., R. A.; Johnston, K. P. Micron Sized Biodegradeable Particles of Poly(L-lactic acid) via the Gas Antisolvent Spray Precipitation Process. Biotechnology Progress. 1993, 9, 429] and methylprednisolone acetate particles (<5 microns) [W. J. Schmitt, M. C. S., G. G. Shook, S. M. Speaker. Finely-Divided Powders by Carrier Solution Injection into a Near or Supercritical Fluid., Am. Inst. Chem. Eng. J. 1995, 41, 2476–2486]. Somewhat surprisingly, the particle sizes have been as small as those made by rapid expansion from a supercritical solution, despite the potentially faster times for depressurization in rapid expansion from a supercritical solution versus two-way mass transfer in the compressed fluid antisolvent process. Not only can the compressed fluid antisolvent process produce PS particles, but also solid and hollow fibers, highly oriented microfibrils, biocontinuous networks, and 100 nm microballoons with porous shells.

To date, it has not been possible to make submicron particles by the compressed fluid antisolvent process without particle aggregation or flocculation. Our objective is to overcome this limitation with the use of surface modifiers, also termed surfactant stabilizers, such as phospholipids, salts of cholic and deoxycholic acids, Tweens (polyoxyethylene sorbitan esters), PLURONIC F-68, TETRONIC 908, hydroxypropylmethyl cellulose (HPMC), TRITON X-100, cetyltrimethylammonium bromide, PEG-400 or combinations of these compounds as described in more detail above.

Considerable variations as to the identities and types of phospholipid and especially the surface active agent or agents should be expected depending upon the water-insoluble or poorly water-soluble biologically active substance selected as the surface properties of these small particles are different. The most advantageous surface active agent for the insoluble compound will be apparent following empirical tests to identify the surfactant or surfactant system/combination resulting in the requisite particle size and particle size stability on storage over time.

Appropriate choice of stabilizers will prevent flocculation in the aqueous phase. The surfactant is chosen to be active at the compound water interface, but it is not chosen to be active at the carbon dioxide-organic solvent or carbon dioxide-drug interface. It is not necessary for the stabilizer to be soluble in $CO_2$; it can be soluble in the liquid to be sprayed, as it only needs to be active at the $CO_2$/solute interface.

This invention provides a supercritical fluid/compressed fluid based process to produce suspensions of water insoluble drugs with an average particle size of less than 100 nm and a narrow size distribution. An essential element is the use of phospholipids and other surfactants to modify the surface of the drug particles to prevent particle aggregation and thereby improve both their storage stability and pharmacokinetic properties.

DETAILED DESCRIPTION OF THE INVENTION

Materials and methods: Particle sizing was based on the principle of photon correlation spectroscopy using Submicron Particle Sizer-Autodilute Model 370 (NICOMP Particle Sizing Systems, Santa Barbara, Calif.). This instrument provides number weighted, intensity weighted, and volume weighted particle size distributions as well as multimodality of the particle size distribution, if present.

Separation and quantitation of cyclosporine was carried out with a Waters HPLC system utilizing reverse phase chromatography. The drug was extracted from the sample with methanol and injected for analysis on a C-18 analytical column at 60–80° C. with a mobile phase consisting of acetonitrile, methanol, and water. Analyte was detected though its absorbance at 214 nm. Operation of the chromatography system and data processing was conducted by Waters Millennium v2.1 software.

Carbon dioxide was used to prepare rapid expansion supercritical solutions since there is no literature reference to any chemical interaction with cyclosporine. Carbon dioxide has been used as a solvent for cyclosporine in fermentation recovery and in HPLC. The relative solubilities of cyclosporine dissolved in a solvent that is expanded with compressed carbon dioxide will be established.

A gas will approach sonic terminal velocity when expanded in a nozzle. Therefore it is important to determine the maximum nozzle diameter and aspect ratio (L/D) that will maintain these conditions in scaleup. Nozzle diameters of 10–50 microns are reported to be used in conjunction with aspect ratios ranging from 5 to 200.

The apparatus for rapid expansion from supercritical solution shown in FIG. 1 included a high pressure vessel 1 for formulating the drug/$CO_2$ solution. Because the drug solution was isolated from the pressurizing fluid by the piston 2 and the valve 2a, the concentration of the drug was constant during the spray. The solution was mixed with a stir bar 14a and a magnetic stirrer 14. The temperature was controlled with heating tape 4. The pressure on the piston and hence the drug solution was controlled via line 3 by an automated syringe pump 5 (ISCO model 100DX) containing pure carbon dioxide.

Figure 2A:
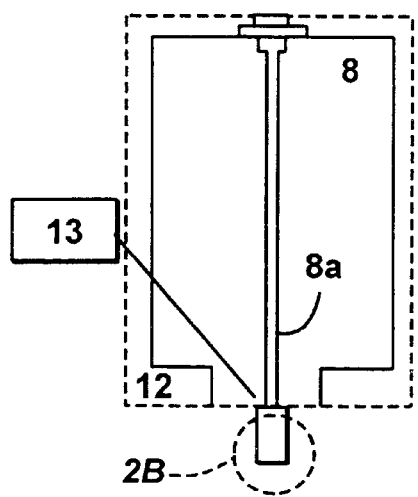
FIG. 2A is a more detailed representation of the preheater assembly of FIG. 1.

The preheater as shown in FIG. 2A consisted of a hole (0.030" i.d. and 4" long) 8a bored axially along the center of a 2" o.d.×0.030" i.d.×4" long copper rod to preheat the solution to a desired temperature before expansion. The preheater assembly 8 and the expansion valve 7 are connected to the high pressure vessel 1 via outlet tube 6. The assembly 8 and the expansion valve 7 were heated with high temperature heating tape 12 and were highly insulated. To monitor the temperature, a thermocouple 13 was placed directly into the preheater assembly close to the orifice.

Figure 2B:
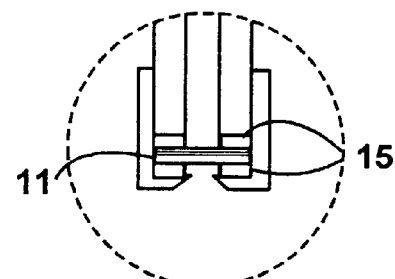
FIG. 2B is an enlarged perspective view of the expansion nozzle of FIG. 1.

The expansion nozzle as shown in more detail in FIG. 2B included a 0.254 mm thick, 30 micron diameter laser-drilled orifice 11 (length to diameter ratio ~8.5), which was placed between two copper gaskets 15 (10 mm o.d., 6 mm i.d. and 1 mm thick) and sealed in a ¼" tubing assembly. The downstream end of the orifice was counterbored into a V-shape as shown in FIG. 2B to prevent the expanding jet from hitting the walls and distorting the morphology of the precipitating solute. To prevent plugging of the orifice, a ¼ inch diameter, 0.5 micron metal filter 9 was inserted upstream of the nozzle preheater assembly (FIG. 1). In addition, a bypass line 10 was used to pre-pressurize the preheater assembly with pure solvent ($CO_2$) before each spray, otherwise the initial pressure drop across the filter would precipitate the drug and plug the orifice 11. After displacing pure solvent from the preheater, the orifice was submerged into 25 mL aqueous solution in order to trap and stabilize the precipitating drug microparticles. The high kinetic energy of the jet forced the spray 2 cm below the surface of the aqueous phase.

Figure 3:
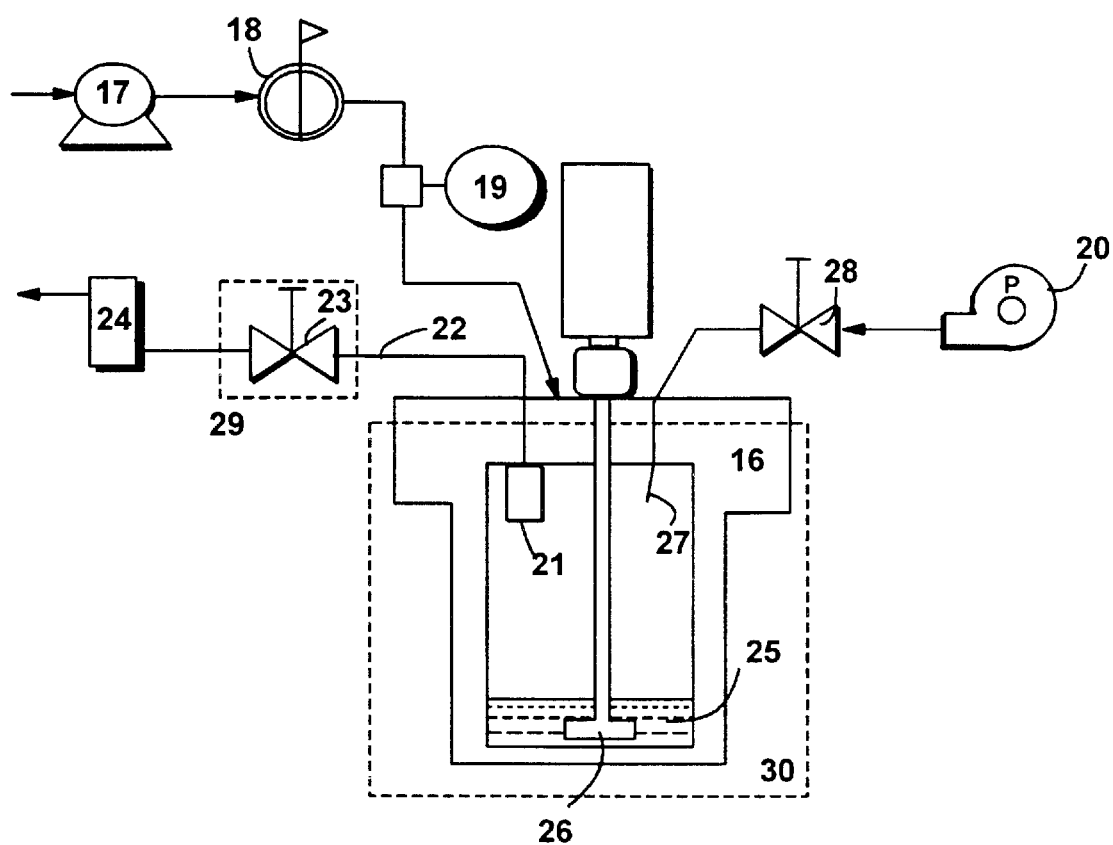
FIG. 3 is a schematic representation of an apparatus for preparing sub-micron sized particles according to the invention by precipitating a bioactive substance, suitably solubilized, into a compressed gas, liquid or supercritical fluid.

The apparatus used to carry out the compressed fluid antisolvent sprays is shown in FIG. 3. A 300 mL high pressure vessel 16 equipped with a magnetically coupled agitator (Parr) depicted in outline above vessel 16 was used to precipitate the drug. Prior to spraying the drug solution, 50 mL of an aqueous medium was added to this precipitator. The aqueous medium was either pure water, 1.0 wt % TWEEN 80 in water, 10 wt % phospholipid dispersion in water or 10 wt % phospholipid dispersion with 2.0 wt % TWEEN 80 in water. Phospholipid and phospholipid plus TWEEN 80 dispersions were made by high shear homogenization of their aqueous suspension by passing through a microfluidizer (model M110EH, Microfluidics). TWEEN 80 was purchased from ICI and egg phospholipid was from Pfansthiel. Aqueous sodium hydroxide solution (1N) was used to adjust the pH of these dispersions to 7.5. Carbon dioxide was compressed with a Haskel air driven gas booster 17 (model AC-152), regulated with a Tescom pressure regulator (model 26-1021) 18 and monitored by pressure gauge 19. The $CO_2$ pressure was monitored to within ±0.2 bar. A water bath with a recirculator 30 was used to control the precipitator temperature. The solution was sprayed through 50 micron i.d. fused silica capillary tubing 27 (Polymicro Technology) with a length/diameter ratio of 2800. To maintain a constant flow rate, the solution was pumped through the solution valve 28 to the capillary atomizer using an automated syringe pump 20 (ISCO model 100DX).

A 0.5 $\mu$m filter 21 was threaded into the $CO_2$ effluent line 22 to prevent loss of the water insoluble compound from the precipitation vessel. The filter assembly included an in-line sintered filter element (Swagelok "F" series ) which was welded onto a ¼" i.d. NPT fitting. The effluent vent valve 23 (Whitey, SS-21RS4) connected to rotameter 24 was heated in a water bath 29 to at least 50° C. to prevent the expanding $CO_2$ from freezing. During precipitation, a known amount of aqueous solution 25 was agitated using a 45° pitched blade impeller 26. After precipitation, agitation was discontinued and the vessel was isolated to depressurize for 30–45 min. The aqueous solution was then recovered for particle size analysis.

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers ($\mu$m=$10^{-6}$ meters), nanometers (nm=$10^{-9}$ meters) or Angstrom units (=0.1 nm). Volumes are given in liters (L), milliliters (mL=$10^{-3}$ L) and microliters ($\mu$L=$10^{-6}$ L). Dilutions are by volume. All temperatures are reported in degrees Celsius. The compositions of the invention can comprise, consist essentially of or consist of the materials set forth and the process or method can comprise, consist essentially of or consist of the steps set forth with such materials.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The following examples further explain and illustrate the invention:

EXAMPLE 1

Figure 4:
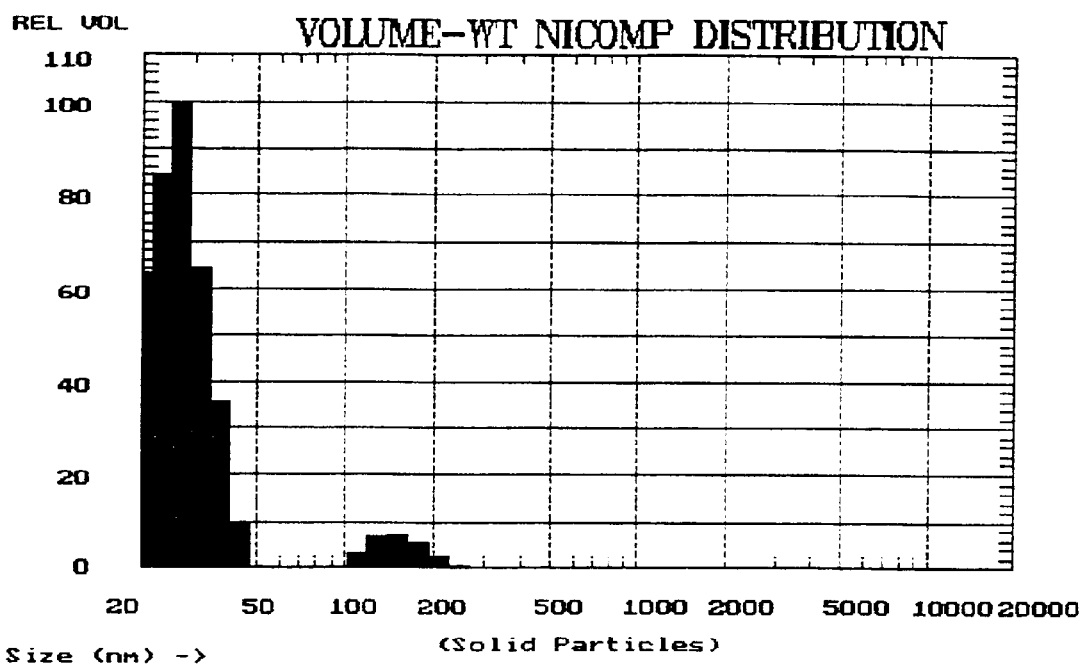
FIG. 4 is a graph showing the particle size distribution on a volume weighted basis of the cyclosporine particles produced in Example 1 expanded into a phospholipid containing 1 wt % stabilizer.
Figure 5:
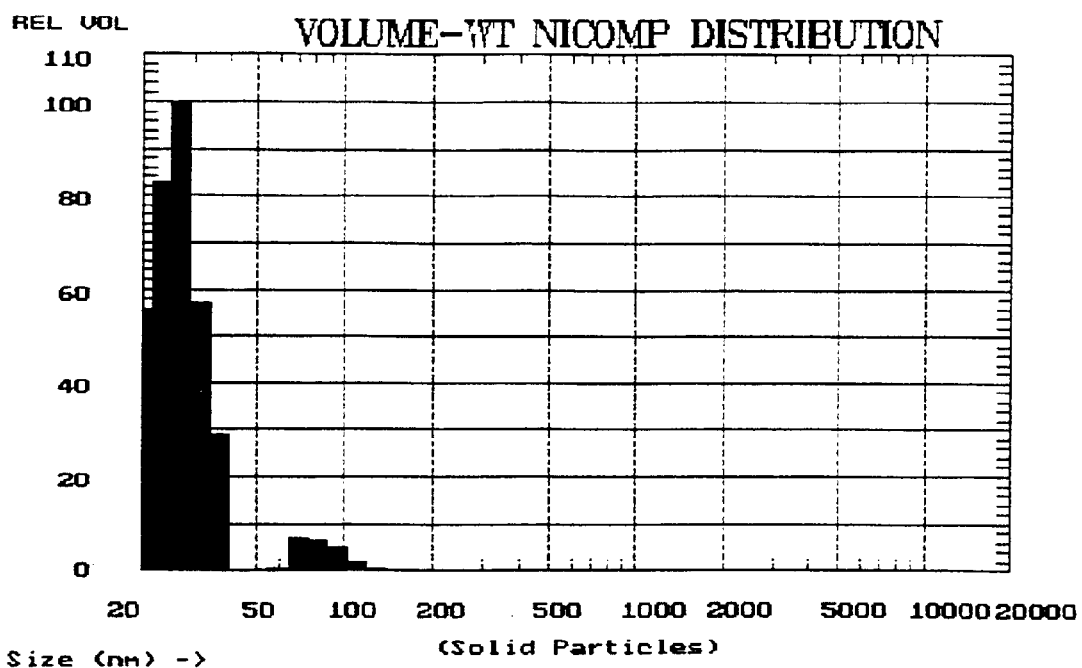
FIG. 5 is a graph showing the particle size distribution on a volume weighted basis of the cyclosporine particles produced in Example 1 expanded into a phospholipid containing 2 wt % stabilizer.

Cyclosporine Microparticle Formation by the Rapid Expansion From Supercritical Solution Process A homogeneous solution of cyclosporine in supercritical $CO_2$ was expanded by rapid expansion from supercritical solution into various aqueous media to study microparticle stabilization. The aqueous media were pure water, 1.0 wt % TWEEN 80, phospholipid dispersion, and 2.0 wt % TWEEN 80 with phospholipid dispersion. 0.0480 g of cyclosporine was charged to a variable volume view cell and 20 mL of $CO_2$ were added to formulate a 0.25 wt % solution. After the solution came to thermal equilibrium (T=35° C.), the cyclosporine/$CO_2$ solution at 3000 psia was sprayed through a 0.30 $\mu$m orifice (L/D of 8) into an aqueous solution for 25 seconds. The pre-expansion temperature was 40° C. The volume weighted particle size of the cyclosporine microparticles expanded into pure phospholipid was 153.7 nm (peak 2) as shown in FIG. 4. Most of the mass that constitutes the peak 1 of 20–50 nm diameter may originate largely from the phospholipid; however, this population may also possess some particles that contain cyclosporine. The volume weighted mean particle size of the cyclosporine microparticles expanded into phospholipid dispersion with 2.0 wt % TWEEN 80 was 80.9 nm (peak 2) as shown in FIG. 5. In this case again the smaller peak (26.8 nm) may originate largely from the phospholipid and TWEEN 80 dispersion and a small fraction of cyclosporine containing particulates. A control experiment was performed in which pure carbon dioxide at 3000 psia was sprayed into the phospholipid dispersion. The mean diameter of the particulates in the dispersion was 9 nm. Therefore, the particles greater than 100 nm in FIGS. 4 and 5 were not originating from purely the phospholipids, but were drug microparticles. Similarly, for the phospholipid dispersion with 2 wt % TWEEN 80, the mean diameter of the particulates was 28 nm.

EXAMPLE 2

Water Insoluble Compound Phase Behavior in Compressed $CO_2$

In order to assess whether a particular water insoluble compound should be processed by rapid expansion from supercritical solution or compressed fluid antisolvent, the solubility of the candidate drugs in carbon dioxide was measured. Cyclosporine, nifedipine, piroxicam, carbamazepine, indomethacin and tetracaine HI were studied. To prepare solutions with a constant molar composition, measured amounts of drug and $CO_2$ were charged to the variable volume view cell from Example 1. To increase the solubility, a cosolvent, i.e., acetone or ethanol, was added to the view cell. The temperature and pressure were varied from 25–45° C. and 1200 to 4500 psia, respectively. The phase behavior was determined visually by noting when phase separation occurred as the pressure was slowly reduced at 1–2 psia/sec. Table 1 shows a summary of the solubility behavior in $CO_2$. Cyclosporine was soluble in $CO_2$ up to 0.5 wt %. Solutions containing 0.01 wt % carbamazepine, tetracaine HI, nifedipine and piroxicam were insoluble in $CO_2$. With the addition of 2.40 wt % acetone, 0.026 wt % piroxicam was soluble in $CO_2$ at 25° C. for all pressures down to the vapor pressure of $CO_2$, which is 930 psia. A solution containing 0.028 wt % nifedipine and 2.26 wt % acetone cosolvent was insoluble in $CO_2$ at 25° C. At 45° C., the nifedipine was solvated with no visible phase separation down to 2000 psia.

| SOLUTE | CONC. (wt %) | TEMP. (° C.) | CLOUD POINT (psia) |
|---|---|---|---|
| Cyclosporine | 0.25 | 25 | soluble down to 1200 |
| Cyclosporine | 0.25 | 30 | 1850 |
| Cyclosporine | 0.25 | 35 | 2060 |
| Piroxicam | 0.069 | 25 | insoluble up to 4500 |
| Nifedipine | 0.088 | 25 | insoluble up to 4000 |
| Nifedipine | 0.029 (a) | 25 | insoluble up to 3500 |
| Carbamazepine | 0.0085 | 25, 40 | insoluble up to 4500 |
| Tetracaine HI | 0.0097 | 25, 45 | insoluble up to 4500 |
| Indomethacin | 0.0098 | 25 | insoluble up to 4000 |

(a) with 2.0% ethanol as a co-solvent.

EXAMPLE 3

Figure 6:
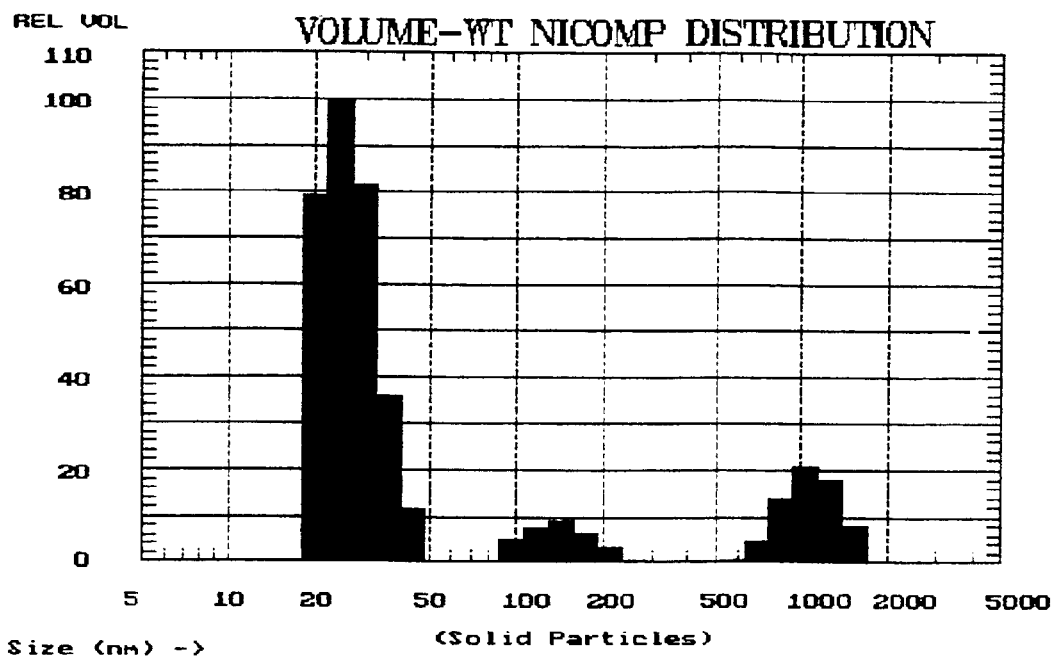
FIG. 6 is a graph showing the particle size distribution on a volume weighted basis of the indomethacin particles produced in Example 3 sprayed directly into carbon dioxide.
Figure 7:
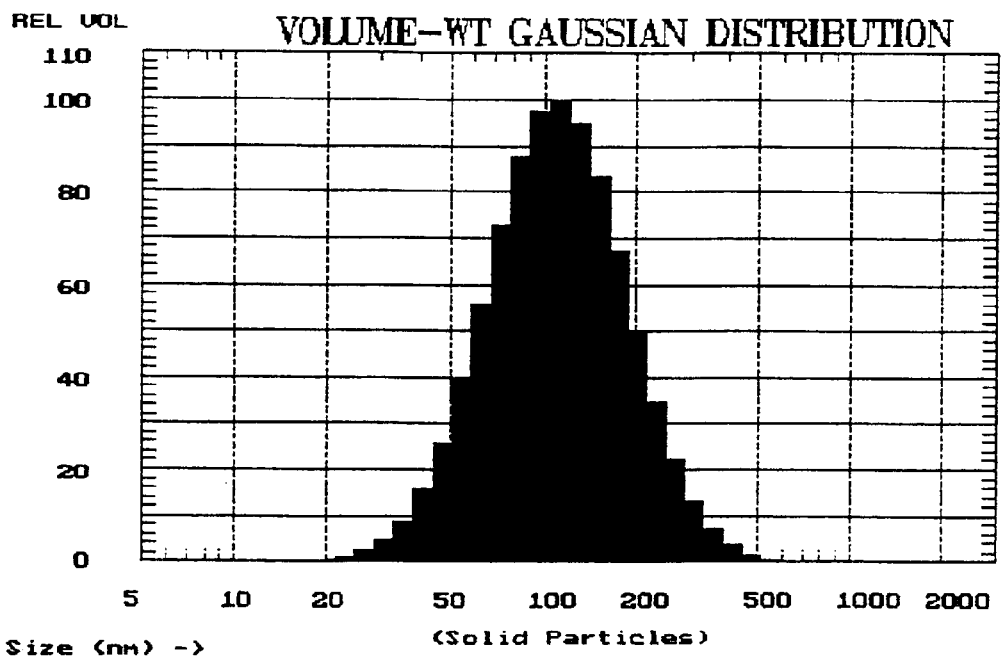
FIG. 7 is a graph showing the particle size Gaussian distribution on a volume weighted basis of the indomethacin particles produced in Example 3 sprayed into a phospholipid containing 2 wt % stabilizer.

Indomethacin Microparticle Formation by the Compressed Fluid Antisolvent Process A 9.9 wt % solution of indomethacin in acetone was sprayed into carbon dioxide with the aqueous solution using the compressed fluid antisolvent process. The duration of the spray was 30 s at 1 mL/min. The volume weighted mean particle size of the phospholipid dispersion was 26 nm (peak 1) as shown in FIG. 6. A bimodal size distribution was observed for the indomethacin particles with mean diameters of 143.0 nm (peak 2) and 1088.9 nm (peak 3), respectively. Particles with such a size difference are easily separated by filtration. For the microparticles precipitated into phospholipid dispersion in the presence of 2.0 wt % TWEEN 80, the volume weighted mean particle diameter was 126 nm as shown in FIG. 7.

EXAMPLE 4

Figure 8:
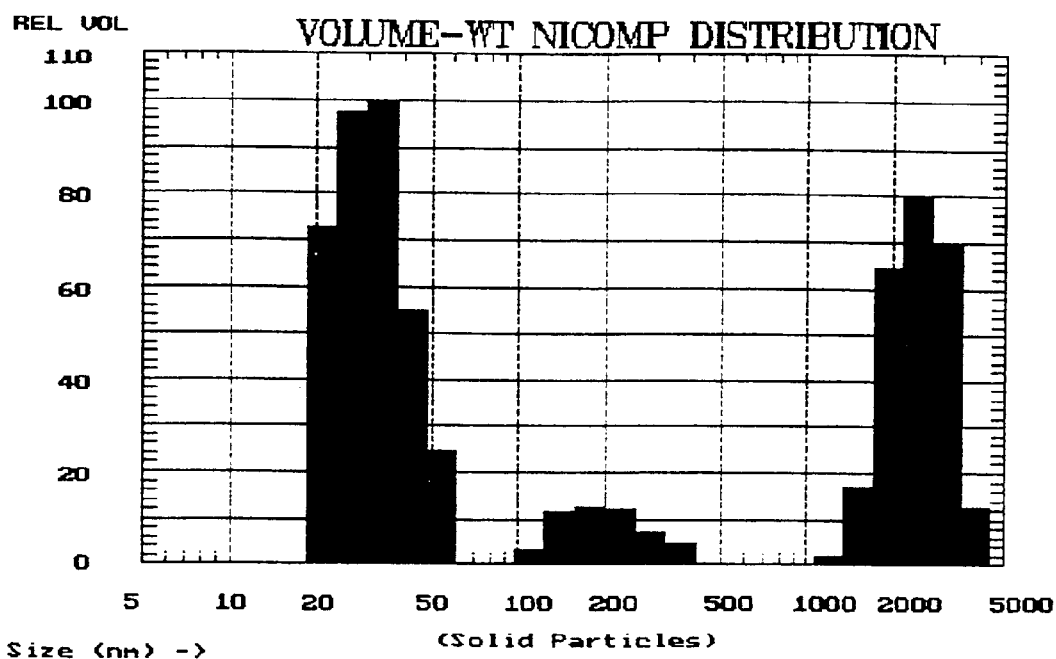
FIG. 8 is a graph showing the particle size distribution on a volume weighted basis of the tetracaine hydrochloride particles produced in Example 4 sprayed into carbon dioxide and water.
Figure 9:
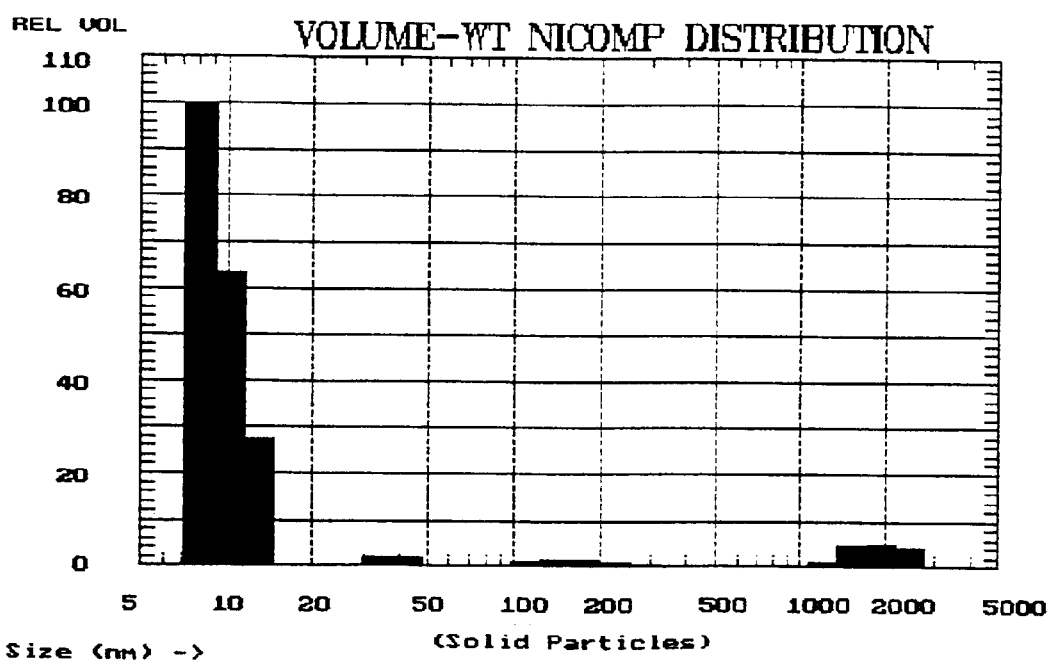
FIG. 9 is a graph showing the particle size distribution on a volume weighted basis of the tetracaine hydrochloride particles produced in Example 4 sprayed into carbon dioxide and water also containing 1 wt % of stabilizer.
Figure 10:
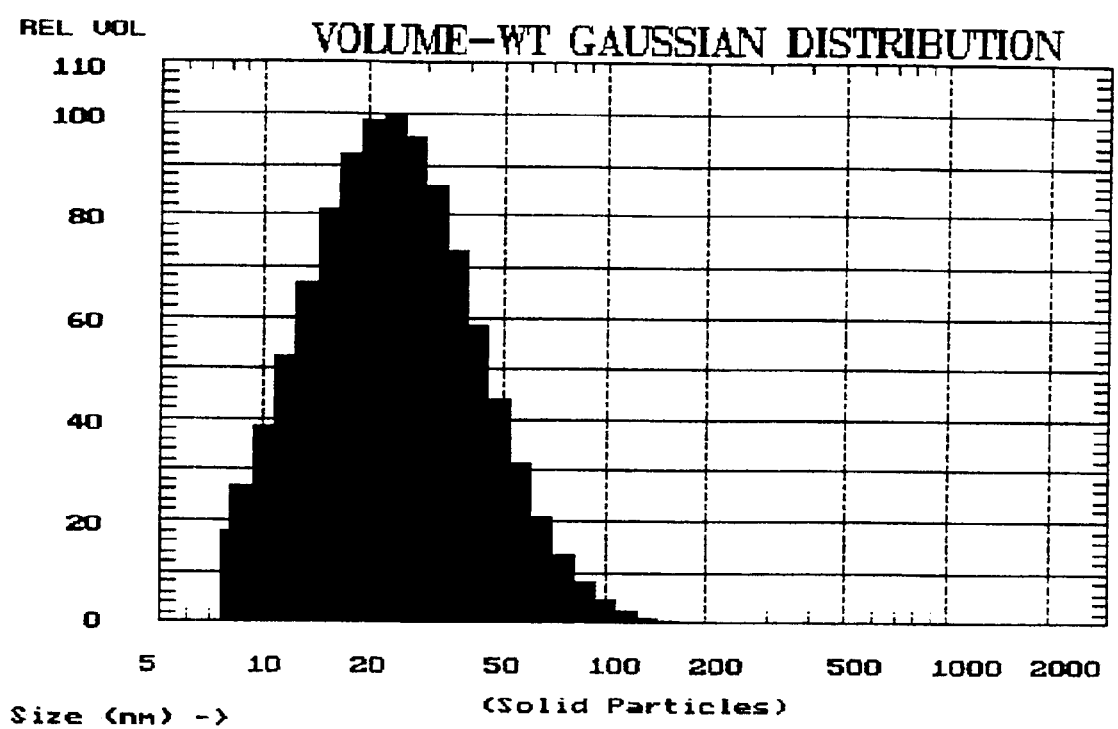
FIG. 10 is a graph showing the particle size Gaussian distribution on a volume weighted basis of tetracaine hydrochloride particles produced in Example 4 sprayed into carbon dioxide, water and 2 wt % stabilizer.

Tetracaine HI Microparticle Formation by the Compressed Fluid Antisolvent Process A 0.97 wt % solution of Tetracaine HI in acetone was sprayed into the precipitator containing carbon dioxide and pure water. The volume weighted mean particle sizes of the Tetracaine HI microparticles were 31.8, 193.4 and 2510.1 nm, respectively (FIG. 8). This illustrates that the compressed fluid antisolvent process can produce extremely small particles even without surfactant stabilizer. With 1.0 wt % TWEEN 80 added to the water, three peaks were observed with mean diameters of 9.5 nm, 38.3 nm and 169.1 nm (FIG. 9). The particle size distribution for 1.0 wt % Tetracaine HI stabilized with phospholipid dispersion and 2.0 wt % TWEEN 80 is shown in FIG. 10. A monomodal distribution is observed between 8–200 nm with a mean diameter of 27.3 nm. This peak includes both the surfactant aggregates and drug particles. No drug particles above 200 nm were observed.

What is claimed is:

1. A process of preparing a surface modifier-stabilized aqueous suspension of submicron sized surface modified microparticles with an average particle size up to 300 nm and a narrow size distribution, wherein 99% of the microparticles produced are below 500 nm, without particle aggregation or flocculation of a water-insoluble or substantially water-insoluble biologically active compound, said process comprising:

(1) dissolving a water-insoluble or substantially water-insoluble biologically active compound in a solvent for said biologically active compound to form a solution; and (2) spraying the solution prepared in (1) into a compressed gas, compressed liquid or supercritical fluid miscible with said solution but antisolvent for said water-insoluble compound in the presence of an agitated aqueous phase and a surface modifier which may be present in said agitated aqueous phase or in a compressed gas, compressed liquid or supercritical fluid or both.

2. A process of preparing a surface modifier-stabilized aqueous suspension of submicron sized surface modified microparticles with an average particle size up to 300 nm and a narrow size distribution, wherein 99% of the microparticles produced are below 500 nm, without particle aggregation or flocculation of a water-insoluble or substantially water-insoluble biologically active compound, said process comprising:

(1) dissolving a water-insoluble or substantially water-insoluble biologically active compound in a compressed fluid to form a solution;

(2) preparing an agitated aqueous phase containing a surface modifier; and (3) spraying the compressed fluid solution of (1) into the agitated aqueous phase of (2).

3. The process according to claim 1, including recovering the microparticles.

4. The process according to claim 1, wherein the surface modifier is a phospholipid.

5. The process according to claim 1, wherein the surface modifier is a surfactant.

6. The process according to claim 1, wherein the surface modifier is a mixture of two or more surfactants.

7. The process according to claim 1, wherein the surface modifier is a polyoxyethylene sorbitan fatty acid ester, a block copolymer of ethylene oxide and propylene oxide, a tetrafunctional block copolymer derived from sequential addition of ethylene oxide and propylene oxide to ethylenediamine, an alkyl aryl polyether sulfonate, polyethylene glycol, hydroxypropylmethylcellulose, sodium dodecylsulfate, sodium deoxycholate, cetyltrimethylammonium bromide, or any combination thereof.

8. The process according to claim 1, wherein the surface modifier is an egg or plant phospholipid or a phospholipid selected from the group consisting of phosphatidylcholine, fully hydrogenated soy lecithin having a minimum 90% phosphatidycholine content, dimyristoyl phosphatidylglycerol, phosphatidylethanolamine, phosphatidylserine, phosphatidic acid, lysophospholipids, salts, and partially or fully hydrogenated forms of these phospholipids, and combinations thereof.

9. The process according to claim 1, wherein the compound is a cyclosporine, indomethacin or tetracaine.

10. The process according to claim 1, wherein the microparticles are less than 100 nm in size.

11. The process according to claim 1, wherein the microparticles range from 5 nm up to about 50 nm in size.

12. The process according to claim 1, wherein 99% of the microparticles are below 400 nm with peaks at half width at half height at about 200 nm.

13. The process according to claim 12, wherein the peaks are below 100 nm.

14. The process according to claim 1, wherein the compressed gas, compressed liquid or supercritical fluid is carbon dioxide.

15. The process according to claim 2, wherein the compressed fluid solution sprayed in (3) is sprayed through a capillary orifice.

16. The process according to claim 1, wherein the surface modifier is a natural, semi-synthetic or synthetic phospholipid.

17. The process according to claim 16, wherein the phospholipid is in partly or fully hydrogenated form.

18. The process according to claim 16, wherein the phospholipid is in desalted or salt form.

19. A process of preparing a surface modifier-stabilized aqueous suspension of surface modified microparticles comprising:
   (1) dissolving a water-insoluble or substantially water-insoluble biologically active compound in a solvent for said biologically active compound to form a solution; and
   (2) spraying the solution prepared in (1) into a compressed gas, compressed liquid or supercritical fluid miscible with said solution but antisolvent for said compound in the presence of an aqueous phase containing a surface modifier.

20. The process according to claim 19, wherein the aqueous phase comprises an agitated aqueous phase.

21. The process according to claim 19, wherein the microparticles are less than 500 nm in size.

22. The process according to claim 21, wherein the microparticles are less than 300 nm in size.

23. The process according to claim 22, wherein the microparticles are less than 100 nm in size.

24. The process according to claim 23, wherein the microparticles range from 5 up to about 50 nm in size.

25. The process according to claim 21, wherein 99% of the microparticles are below 400 nm with peaks at half width at half height at about 200 nm.

26. The process according to claim 25, wherein the peaks are below 100 nm.

27. The process according to claim 19, including recovering the microparticles from the aqueous suspension.

28. The process according to claim 19, wherein the surface modifier is a phospholipid.

29. The process according to claim 19, wherein the surface modifier is a surfactant.

30. The process according to claim 19, wherein the surface modifier is a mixture of two or more surfactants.

31. The process according to claim 19, wherein the surface modifier is a polyoxyethylene sorbitan fatty acid ester, a block copolymer of ethylene oxide and propylene oxide, a tetrafunctional block copolymer derived from sequential addition of ethylene oxide and propylene oxide to ethylenediamine, an alkyl aryl polyether sulfonate, polyethylene glycol, hydroxypropylmethylcellulose, sodium dodecylsulfate, sodium deoxycholate, cetyltrimethylammonium bromide or any combination thereof.

32. The process according to claim 19, wherein the surface modifier is natural, semi-synthetic or synthetic phospholipid, in fully or partially hydrogenated form, and in desalted or salted form.

33. The process according to claim 32, wherein the phospholipid is an egg or plant phospholipid.

34. The process of claim 32, wherein the surface modifier is a phospholipid selected from the group consisting of phosphatidylcholine, fully hydrogenated soy lecithin having a minimum 90% phosphatidycholine content, dimyristoyl phosphatidylglycerol, phosphatidylethanolamine, phosphatidylserine, phosphatidic acid, lysophospholipids, their salts, partially or fully hydrogenated forms, and combinations thereof.

35. The process according to claim 19, wherein the compound is a cyclosporine, indomethacin or tetracaine.

36. The process according to claim 19, wherein the compressed gas or compressed fluid is gas, liquid or supercritical carbon dioxide.

37. A process of preparing a surface modifier stabilized aqueous suspension of surface modified microparticles with an average particle size up to 300 nm and a narrow size distribution, wherein 99% of the microparticles produced are below 500 nm comprising:
   (1) dissolving a water-insoluble or substantially water-insoluble biologically active compound in a compressed fluid to form a solution;
   (2) preparing an aqueous phase containing a surface modifier; and
   (3) spraying the compressed fluid solution of (1) into the aqueous phase of (2).

38. The process according to claim 37, wherein the aqueous phase comprises an agitated aqueous phase.

39. The process according to claim 37, wherein the compressed fluid solution sprayed in (3) is sprayed through a capillary orifice.

40. The process according to claim 37, including the additional step of recovering the microparticles so produced.

41. The process according to claim 37, wherein the surface modifier is a natural, semi-synthetic or synthetic phospholipid.

42. The process according to claim 41 wherein the phospholipid is in partly or fully hydrogenated form.

43. The process according to claim 41 wherein the phospholipid is in desalted or salt form.

44. The process according to claim 37, wherein the surface modifier is a surfactant.

45. The process according to claim 37, wherein the surface modifier is a mixture of two or more surfactants.

46. The process according to claim 37, wherein the compound is a cyclosporine, indomethacin or tetracaine.

47. A process of preparing microparticles of a water-insoluble or substantially water-insoluble biologically active compound comprising:
   (1) dissolving a water-insoluble or substantially water-insoluble biologically active compound in a compressed fluid;
   (2) preparing an aqueous phase containing a surface modifier comprising a phospholipid; and (3) spraying the compressed fluid solution of (1) into the aqueous phase of (2) to form microparticles of the compound.

48. The process according to claim 47, wherein the aqueous phase comprises an agitated aqueous phase.

49. The process according to claim 47, wherein the compressed fluid solution is sprayed in (3) through a capillary orifice.

50. The process according to claim 47, wherein the phospholipid is in partly or fully hydrogenated form.

51. The process according to claim 47, wherein the phospholipid is in desalted or salt form.

52. The process according to claim 47, wherein the compressed fluid is gas, liquid or supercritical carbon dioxide.

53. The process according to claim 47, wherein the compound is a cyclosporine, indomethacin or tetracaine.

54. A process of preparing microparticles of a water-insoluble or substantially water-insoluble biologically active compound comprising:
   (1) dissolving a water-insoluble or substantially water-insoluble biologically active compound in a compressed fluid;
   (2) preparing an aqueous phase containing a surface modifier comprising a mixture of two or more surfactants; and
   (3) spraying the compressed fluid solution of (1) into the aqueous phase of (2) to form microparticles of the compound.

55. The process according to claim 54, wherein the aqueous phase comprises an agitated aqueous phase.

56. The process according to claim 54, wherein the compressed fluid solution is sprayed in (3) through a capillary orifice.

57. The process according to claim 54, wherein at least one surfactant is a polyoxyethylene sorbitan fatty acid ester, a block copolymer of ethylene oxide and propylene oxide, a tetrafunctional block copolymer derived from sequential addition of ethylene oxide and propylene oxide to ethylenediamine, an alkyl aryl polyether sulfonate, polyethylene glycol, hydroxypropylmethylcellulose, sodium dodecylsulfate, sodium deoxycholate, cetyltrimethylammonium bromide or any combination thereof.

58. The process according to claim 54, wherein the compressed fluid is gas, liquid or supercritical carbon dioxide.

59. The process according to claim 54, wherein the compound is a cyclosporine, indomethacin or tetracaine.

60. A process of preparing microparticles of a water-insoluble or substantially water-insoluble biologically active compound comprising:
   (1) dissolving a water-insoluble or substantially water-insoluble biologically active compound in a compressed fluid comprising carbon dioxide;
   (2) preparing an aqueous phase containing a surface modifier; and
   (3) spraying the compressed fluid solution of (1) into the aqueous phase of (2) to form microparticles of the compound.

61. The process according to claim 60, wherein the aqueous phase comprises an agitated aqueous phase.

62. The process according to claim 60, wherein the compressed fluid solution sprayed in (3) is sprayed through a capillary orifice.

63. The process according to claim 60, wherein the compound is a cyclosporine, indomethacin, or tetracaine.

64. The aqueous suspension prepared by the process of claim 1.

65. The aqueous suspension prepared by the process of claim 2.

66. The aqueous suspension prepared by the process of claim 19.

67. The aqueous suspension prepared by the process of claim 37.

68. The microparticles prepared by the process of claim 47.

69. The microparticles prepared by the process of claim 54.

* * * * *